US005501970A

United States Patent [19]

Legname et al.

[11] Patent Number: 5,501,970
[45] Date of Patent: Mar. 26, 1996

[54] NUCLEOTIDE SEQUENCES CODING FOR RIBOSOME INACTIVATING PROTEINS

[75] Inventors: Giuseppe Legname; Gianni Gromo; Daniela Modena; Diego Brocchetti, all of Milan, Italy

[73] Assignee: ITALFARMACO S.p.A., Milan, Italy

[21] Appl. No.: 182,114

[22] PCT Filed: Jul. 29, 1992

[86] PCT No.: PCT/EP92/01711

§ 371 Date: May 13, 1994

§ 102(e) Date: May 13, 1994

[87] PCT Pub. No.: WO93/03153

PCT Pub. Date: Feb. 18, 1993

[30] Foreign Application Priority Data

| | | | |
|---|---|---|---|
| Jul. 31, 1991 | [IT] | Italy | MI91A02136 |
| Jun. 17, 1992 | [IT] | Italy | MI92A01476 |

[51] Int. Cl.$^6$ .......................... C12N 15/29; C12N 15/56; C12N 1/21; C12N 5/10; C12N 15/63

[52] U.S. Cl. .................................... 435/240.1; 435/252.3; 435/252.33; 435/320.1; 435/200; 536/23.2

[58] Field of Search ............................ 435/320.1, 252.3, 435/252.33, 69.1, 200, 240.1; 536/23.2

[56] References Cited

U.S. PATENT DOCUMENTS 5,317,009 5/1994 Lee-Huang et al. ........................ 514/8

FOREIGN PATENT DOCUMENTS 04025544 12/1990 European Pat. Off. .

OTHER PUBLICATIONS

Falasca et al. (1982) Biochem J. 207:505–509.

Legname et al. (1991) Biochim. Biochim. Biophys. Acta 1090: 119–122.

*Primary Examiner*—Robert A. Wax

*Assistant Examiner*—G. E. Bugaisky

*Attorney, Agent, or Firm*—Oblon, Spivak, McClelland, Maier & Neustadt

[57] ABSTRACT

This invention refers to DNA sequences coding for proteins present in the plant *Dianthus caryophyllus*, to expression vectors containing said sequences and to hosts transformed by said vectors.

8 Claims, 3 Drawing Sheets

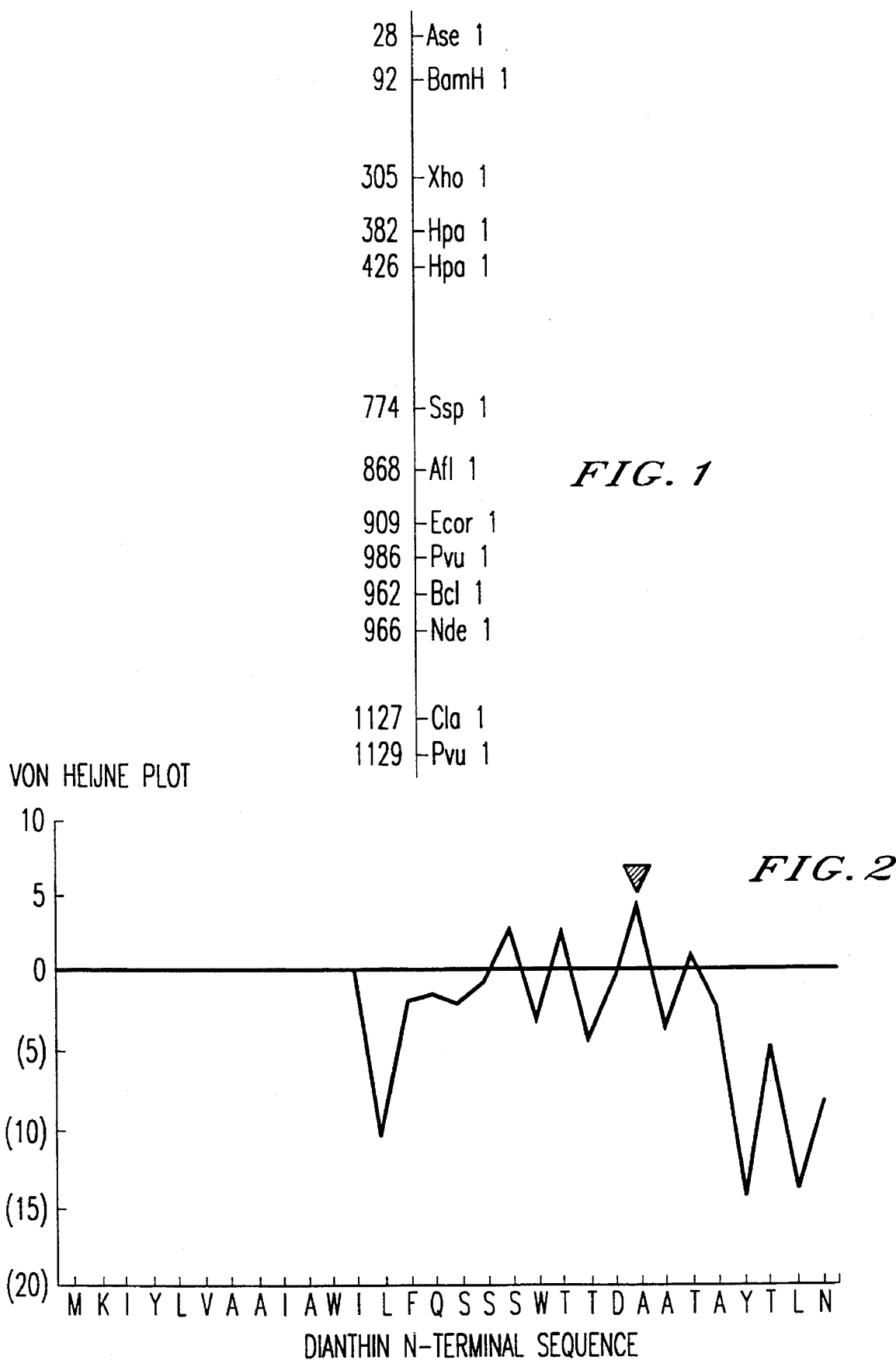

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 879 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Dianthus caryophyllus ( x i ) SEQUENCE DESCRIPTION: SEQ ID NO:1:

| | | | | | |
|---|---|---|---|---|---|
| ATGAAGATTT | ATTTAGTGGC | CGCGATAGCA | TGGATCCTGT | TTCAGTCTTC | ATCTTGGACA | 60
| ACTGATGCGG | CCACAGCATA | CACATTAAAT | CTCGCAAATC | CATCCGCGAG | TCAATACTCA | 120
| TCTTTTCTGG | ATCAAATCCG | AAACAATGTG | AGGGATACCA | GCCTCATATA | CGGTGGGACA | 180
| GACGTAGCCG | TGATTGGTGC | GCCTTCTACT | ACTGATAAAT | TCCTTAGACT | TAATTTCCAA | 240
| GGTCCTCGAG | GAACGGTCTC | TCTTGGCCTT | AGGCGCGAGA | ACTTATACGT | GGTCGCGTAT | 300
| CTTGCAATGG | ATAACGCAAA | TGTTAACCGT | GCATATTACT | TCAAAAACCA | AATCACTTCT | 360
| GCTGAGTTAA | CCGCCCTTTT | CCCCGAGGTT | GTGGTTGCAA | ATCAAAAACA | ATTAGAGTAC | 420
| GGGGAAGATT | ACCAGGCGAT | AGAAAAGAAC | GCCAAGATAA | CAACAGGCGA | TCAAAGTAGA | 480
| AAGGAACTCG | GTTTGGGGAT | CAATCTACTT | ATAACGATGA | TTGATGGAGT | GAATAAGAAG | 540
| GTACGTGTAG | TCAAAGACGA | GGCAAGGTTT | TTGTTAATCG | CAATTCAAAT | GACGGCTGAG | 600
| GCCGCGCGAT | TTAGGTACAT | ACAGAACTTG | GTTACCAAGA | ACTTCCCAAA | CAAGTTCGAC | 660
| TCAGAAAATA | AGGTTATTCA | ATTTCAAGTT | AGTTGGAGTA | AGATTTCTAC | GGCAATATTT | 720
| GGGGATTGCA | AAACGGCGT | GTTTAATAAA | GATTATGATT | TCGGGTTTGG | GAAAGTGAGG | 780
| CAGGCAAAAG | ACCTTCAAAT | GGGGCTCCTT | AAGTATTTAG | GTAGACCGAA | GTCGTCGTCA | 840
| ATCGAGGCGA | ATTCCACTGA | CGACACAGCT | GATGTGCTT | | | 879

( 2 ) INFORMATION FOR SEQ ID NO:2:

( i ) SEQUENCE CHARACTERISTICS:
        ( A ) LENGTH: 813 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Dianthus caryophyllus ( x i ) SEQUENCE DESCRIPTION: SEQ ID NO:2:

| | | | | | |
|---|---|---|---|---|---|
| ATGGCCACAG | CATACACATT | AAATCTCGCA | AATCCATCCG | CGAGTCAATA | CTCATCTTTT | 60
| CTGGATCAAA | TCCGAAACAA | TGTGAGGGAT | ACCAGCCTCA | TATACGGTGG | GACAGACGTA | 120
| GCCGTGATTG | GTGCGCCTTC | TACTACTGAT | AAATTCCTTA | GACTTAATTT | CCAAGGTCCT | 180
| CGAGGAACGG | TCTCTCTTGG | CCTTAGGCGC | GAGAACTTAT | ACGTGGTCGC | GTATCTTGCA | 240
| ATGGATAACG | CAAATGTTAA | CCGTGCATAT | TACTTCAAAA | ACCAAATCAC | TTCTGCTGAG | 300
| TTAACCGCCC | TTTTCCCCGA | GGTTGTGGTT | GCAAATCAAA | AACAATTAGA | GTACGGGGAA | 360
| GATTACCAGG | CGATAGAAAA | GAACGCCAAG | ATAACAACAG | GCGATCAAAG | TAGAAAGGAA | 420
| CTCGGTTTGG | GGATCAATCT | ACTTATAACG | ATGATTGATG | GAGTGAATAA | GAAGGTACGT | 480
| GTAGTCAAAG | ACGAGGCAAG | GTTTTTGTTA | ATCGCAATTC | AAATGACGGC | TGAGGCCGCG | 540
| CGATTTAGGT | ACATACAGAA | CTTGGTTACC | AAGAACTTCC | CAAACAAGTT | CGACTCAGAA | 600
| AATAAGGTTA | TTCAATTTCA | AGTTAGTTGG | AGTAAGATTT | CTACGGCAAT | ATTTGGGGAT | 660
| TGCAAAAACG | GCGTGTTTAA | TAAAGATTAT | GATTTCGGGT | TGGGAAAGT | GAGGCAGGCA | 720
| AAAGACCTTC | AAATGGGGCT | CCTTAAGTAT | TTAGGTAGAC | CGAAGTCGTC | GTCAATCGAG | 780
| GCGAATTCCA | CTGACGACAC | AGCTGATGTG | CTT | | | 813

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:3:

CGCGTCACCA TGGCCACAGC ATACACATTA AATCTCGC    38

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:4:

CCATCTCGAG AAGCTTCATC AAAGCACATC AGCTGTGTC    39

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO ( x i ) SEQUENCE DESCRIPTION: SEQ ID NO:5:

CCGTCGACAG ATCTCAAGAT GAAGATTTAT TTAGTGGC    38

NUCLEOTIDE SEQUENCES CODING FOR RIBOSOME INACTIVATING PROTEINS

This invention refers to DNA sequences coding for proteins present in the plant *Dianthus caryophyllus,* to expression vectors containing said sequences and to hosts transformed by said vectors.

It is widely known that proteins extracted from various plants are able to inhibit protein synthesis of animal cells by inhibiting their ribosomes.

This group of proteins has been classified as ribosome inactivating proteins type 1 and type 2 (RIP 1 and RIP 2 ) according to the numbers of polypeptide chains they are composed of: RIPs 1 have a single polypeptide chain having enzymatic activity causing ribosome modifications; RIPs 2, besides this chain, have a second chain binding to cells with particular receptor molecules.

RIPs 2 are very toxic because of their capacity to bind most intact cells: examples of RIPs 2 are ricin, abrin, modeccin, viscumin. RIPs 1 are practically non-toxic since they cannot bind to cell surface; they need to enter the cytoplasm to exert their enzymatic activity inhibiting the protein synthesis; examples of RIPs 1 are saporin, gelonin, momordin, dianthin 30 and 32. The last two ones may be extracted from different tissues of the plant *Dianthus caryophyllus* wherein they are present in two forms having different molecular weight, respectively 30000 and 32000 Daltons; said molecules seem to be two different proteins although no definitive conclusion has been drawn.

According to their molecular weight, they were named dianthin 30 and 32 (Stirpe et al Biochem. J., 1981, 195, pp. 399–405; Falasca et al Biochem. J., 1982, 207, pp. 505–509). The biochemical characteristics of these two proteins are similar: pI is remarkably basic for both (>9.5 pH units ); kms calculated on rabbit reticulocyte lysate are identical whereas kcat are slightly different, that of dianthin 32 being higher than dianthin 30.

It is known that some proteins are expressed together with signal peptides controlling the targeting of proteins to different organelles. Some signal peptides are cleaved once completed their targeting role and are therefore no longer present in the mature protein.

In the case of dianthin 30, the protein is synthesized as a precursor, pre-dianthin, containing the active sequence preceded by a signal peptide characteristic of the secretion protein, targeting the protein to the endoplasmatic reticulum.

This signal sequence is located at the N-terminus of the polypeptide chain and it is characterized by the presence of hydrophobic amino acids helping the translocation of the protein.

We have cloned and expressed cDNA sequences coding for RIP 1 of *Dianthus caryophyllus,* dianthin 30 and for its precursor pre-dianthin 30.

The DNA sequences of the invention are reported in the Sequence Listings Nos: 1 and 2.

The present invention also relates to DNA sequences that hybridize to the above mentioned DNA sequence and that encode a polypeptide having dianthin-like activity. In this context, the term "hybridization" refers to conventional hybridization conditions.

Most preferably, the term "hybridization" refers to stringent hybridization conditions.

The DNA sequences of the invention may be obtained according to the following method:

(i) isolation of mRNA from tissue of the plant *Dianthus caryophyllus;*

(ii) synthesis of cDNA from mRNA;

(iii) insertion of the resulting cDNA in cloning vector so as to obtain a cDNA library;

(iv) analysis of the cDNA library by oligonuclectides labelled with radioactive phosphorus coding for particular regions of the protein to be identified or by anti-dianthin polyclonal antibodies raised in rabbit so as to identify a clone containing the expressed protein and, finally, (v) isolating the specific DNA sequence present in the previously identified clone;

(vi) subjecting to PCR (Polymerase Chain Reaction) the sequence isolated in (v) so as to amplify only the region coding for either pre-dianthin 30 or for the native protein.

The mRNA is extracted from leaves of *Dianthus caryophyllus.*

The cDNA may be synthesized using commercial kits.

cDNA is inserted in a cloning vector to obtain a cDNA library. The cloning vector may be a plasmid or a bacteriophage.

In the present invention, the lambda gt 11 phage has been used as a cloning vector, in which the different cDNA sequences of the library are inserted in its genome so as to allow the expression of a fusion protein between the beta-galactosidase normally present in the phage and the protein to be cloned.

The expression is made possible using *E. coli* strains particularly sensitive to this phage.

The library is then analyzed with rabbit specific anti-dianthin polyclonal antibodies which can easily detect the presence of the protein even though fused with the phagic beta-galactosidase.

In this way one or more clones can be identified in which the desired DNA sequence coding for the target protein is present. This sequence or longer sequences comprising it may be isolated using a specific endonuclease enzyme.

The isolated DNA sequence may thus be specifically expressed without beta-galactosidase, as a non-fused protein.

In order to obtain the protein product, the isolated DNA sequence is subjected to a PCR so as to amplify only the region coding for the desired protein, inserting suitable restriction sites at both ends of it.

The so obtained DNA sequence is inserted in an expression vector so as to specifically bind to control elements of the expression system.

The vector has a replication origin and a phenotypic marker. Start and stop codons are provided to the DNA sequence to be translated. Plasmidic vectors according to the invention have been deposited according to the Budapest Treaty at the National Collection of Type Cultures under accession numbers NCTC 12477 and NCTC 12693.

NCTC 12477, deposited on 20.6.1991 contains the plasmid pKK-DIA30 comprising the Sequence Listing n° 2 whereas NCTC 12693, deposited on 2.6.1992 contains the cloning vector pGEM-pDIA30 comprising the Sequence Listing No: 1.

The invention will be described with reference to the enclosed drawings, in which:

FIG. 1 shows the restriction map of the sequence of cDNA cloned.

FIG. 2 shows the graph deduced from the yon Heijne algoritm allowing the identification of the first amino acid of the native protein starting from a sequence containing a signal peptide (yon Heijne G. NAR, 1986, 14, pp. 4683–4690).

FIG. 3 shows the expression plasmids pKK-DIA30.

FIG. 4 shows the in vitro expression plasmid pGEM-pDIA 30.

Figure 5:
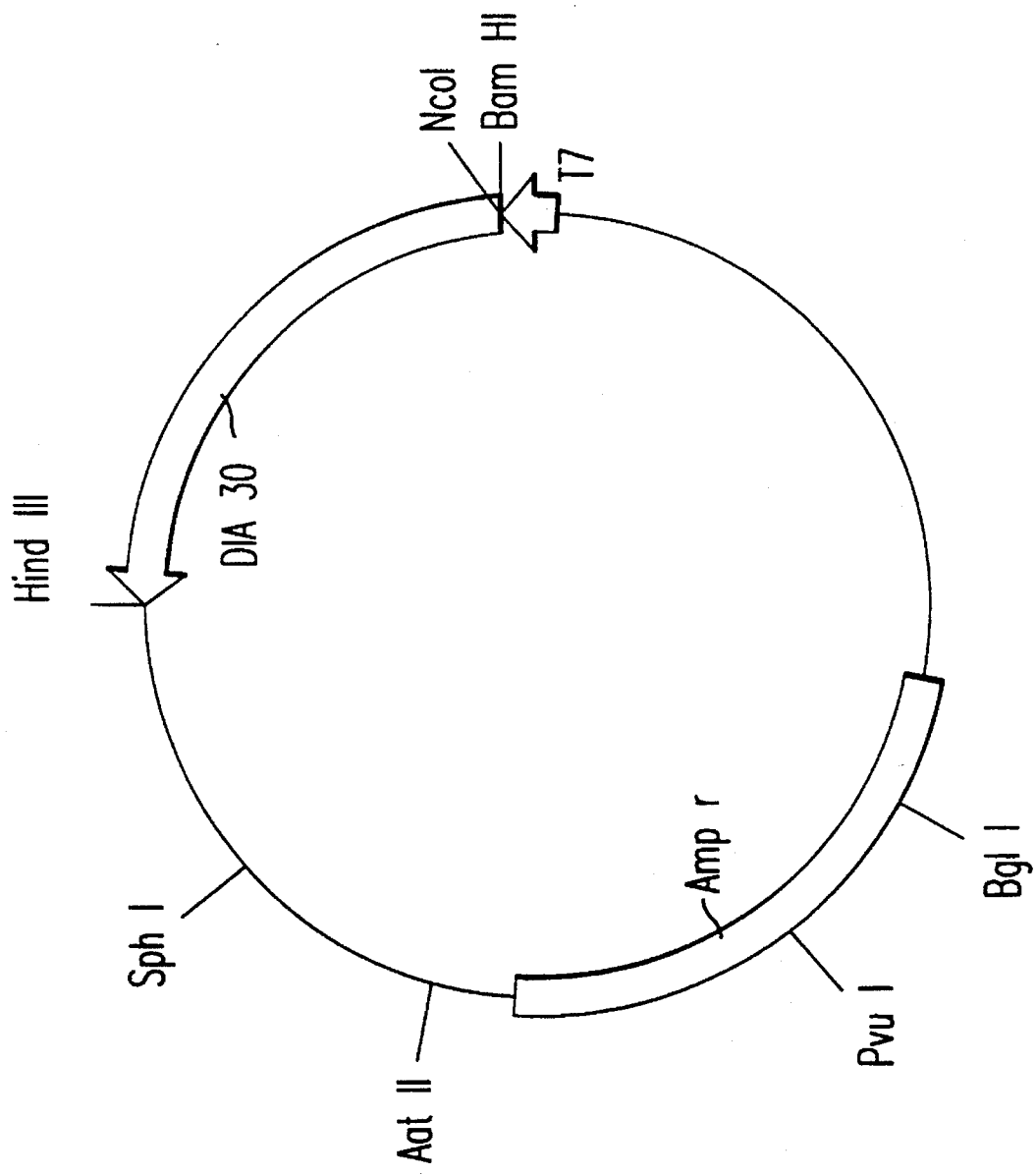

FIG. 5 shows the in vitro expression plasmid pGEM-DIA 30.

EXAMPLE 1 cDNA library mRNA extraction 20 g of frozen carnation leaves were homogenized in a mortar using 60 ml of 200 mM Tris-acetate, 120 mM potassium acetate, 50 mM Mg-acetate, 3.4% saccharose, 0.04% DTT, 0.4% 2'-3' AMP, pH 8 as extraction buffer.

After homogenization the obtained mixture was centrifuged for 20 minutes at 4° C., the surnatant was then extracted three times with the same volume of a 1:1 phenol:chloroform solution. Finally, the extraction sequence was followed by a further extraction with chloroform and the mixture was centrifuged again.

The so obtained aqueous solution, was added with 1/20 volume of 7 M ammonium acetate, mixed and added with 2.5 volumes of absolute ethanol and the so obtained solution was incubated at −80° C. for one hour at least. The resulting mixture was centrifuged at 2500 rpm for 30 minutes at 4° C. and the precipitate was washed with 75% ethanol and centrifuged again. The precipitate was dried and suspended in water and ¼ volume of 10 M lithium chloride was added thereto. This solution was incubated for 12–16 hours at 4° C. After the incubation, the solution was centrifuged at 4000 rpm for 30 minutes at 4° C. It was then re-suspended twice in 75% ethanol, each time followed by a centrifugation at 1000 rpm for 15 minutes at 4° C. The precipitate was dried and re-suspended in water.

8 mM tris-HCl, 1 mM EDTA, 0.1% SDS, 400 nM NaCl, pH 8.5 buffer was then added to the aqueous solution and the mixture was then heated for 5 minutes at 60° C. After incubation, the solution was eluted on a column of oligothymidilic acid-cellulose (Sigma, USA). The polyadenylated mRNA bound to the column was eluted with a 8 mM tris-HCl, 1 mM EDTA, 0.1% SDS, pH 7.9 solution.

The so purified polyadenylated RNA was precipitated for 12–16 hours at 4° C. with 1/20 volume of 7 M ammonium acetate and 2.5 volumes absolute ethanol and centrifuged at 10000 rpm for 15 minutes a 4 ° C., washed twice with 75% ethanol and finally suspended water and stored at −80° C. 20 µg RNA poly(A$^+$) were obtained from 1 µg of total RNA.

cDNA synthesis

The cDNA was synthesized using a commercial kit ("cDNA synthesis system plus", n° RNP 1256 Y/Z, Amersham, UK).

Insertion of cDNA library in lambda gt 11

The cDNA library was inserted in lambda gt 11 using a commercially available kit ("cDNA cloning system—lambda gt 11", n. cat. RPN. 1280, Amersham, Great Britain).

EXAMPLE 2

Analysis of the cDNA library

The analysis of the cDNA library inserted in lambda gt 11 has been substantially carried out as disclosed in Sambrook J. et al Molecular cloning: a laboratory manual. 1989, 12,16–20, except for the processing of the nitrocellulose filters after the binding of the first antibody. This step was carried out using a commercial kit ("Protoblot immuno-screening system", cat. n. P3771 Promega, USA)

DNA sequencing

The DNA of the isolated clone was isolated according to the instructions of the kit "cDNA cloning system—lambda gt 11"; the insert was alternatively removed with EcoRI or with BamI and respectively ligated in the EcoRI or BamHI site of the pUC8 or pUC9 plasmids. The restriction map of the obtained clone is shown in FIG. 1.

The sequencing was carried out according to the method of Sanger, using the Sequenase kit (United States Biochemical Corporation, USA).

The cDNA has been sequenced in both directions, showing an open reading frame of 293 amino acids.

EXAMPLE 3

Expression of the clone coding for dianthin in *E. coli*

Starting from the clone of Example 2 in which the portion coding for dianthin is present, a PCR (kit GeneAmp$^R$) was carried out using specific primers so as to amplify only the region coding for the native protein, deduced by the von Heijne algoritm (FIG. 2) inserting moreover suitable restriction sites at both ends of it, such as NcoI at the 5'-end and HindIII and PstI at the 3'-end (Sequence Listings Nos: 3 and 4).

This was confirmed by protein sequencing.

The reaction mixture was analyzed on a 1% agarose gel wherein a single band of 843 bp was detected. The band was eluted from the gel by means of pre-activated DE81. The paper elution was carried out in a high strength buffer such as 1.5 M NaCl/TB for 2 hours at 37° C. and 2 volumes of ethanol were added to the resulting solution and it was incubated for 12–16 hours at −20° C.

Then, the solution was centrifuged at 13500 rpm for 5 minutes and the precipitate was resuspended in TE. The used expression plasmid was pKK-233.2 containing in its polycloning site three restriction sites, namely NcoI providing the start codon ATG, PstI and HindIII. The fragment and the plasmid were sequentially digested with NcoI and HindIII and then ligated to transform a suitable *E. coli* strain.

Figure 3:
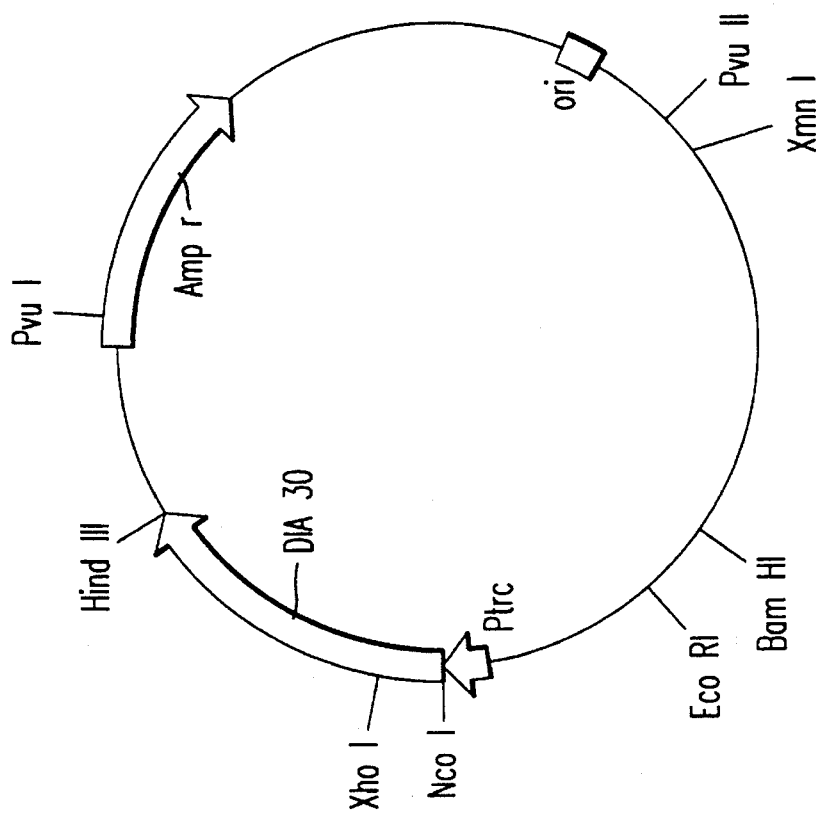

The map of the resulting plasmid, named pKK-DIA30 is shown in FIG. 3. The *E. coli* strain JM109 transformed with the plasmid pKK-DIA30 and was cultured in a minimal medium M9 supplemented with 1 mM thymidine and 100 µg/ml of ampicilline to an OD$_{600}$ of 0.5. The culture was then induced with isopropyl-1βD-galactopyranoside at the final concentration of 1 mM for 3 hours at 30° C. The sonicated cells were centrifuged at 5000 rpm for 10 minutes at 4° C. to remove intact cells. The supernatant was centrifuged at 100.000 g for 1 hour at 2 ° C. The supernatant, containing the soluble proteins, was recovered and the pellet of insoluble proteins was resuspended in 100 mM Tris HCl, 5 mM EDTA, pH 8.5.

The two solutions were analysed by SDS-PAGE and Western blot and the presence of a band of about 30000 Daltons of molecular weight corresponding to recombinant dianthin was checked.

EXAMPLE 4

In vitro transcription-translation of pre-dianthin 30 and dianthin 30

A PCR was carried out on a phagic DNA template of the clone containing the complete sequence of predianthin 30, using specific primers. More particularly, the primer of Sequence Listing No: 5, named pDia 5', is an oligonucleotide 38 base long for the specific amplification of the region of pre-dianthin 30. It comprises two single restriction sites, SalI and BglII, not present in the sequence to be amplified and, downstream of them, the sequence coding for the first 6 amino acid of the polypeptide.

The second oligonucleotide is Dia 5' (Sequence Listing No: 3 ) 38 bases long containing the restriction site NcoI, providing also the start codon ATG, and immediately downstream of it the DNA sequence coding for the first 8 amino acids of the native dianthin 30. The primer of Sequence Listing No: 4 was used in the amplification of DNA fragments coding for both proteins. This primer, named Dia 3' (Sequence Listing No: 4) 39 bases is specific for the nucleotide sequences coding for the last 6 amino acids of the two proteins followed by two stop codons TGA and the restriction sites HindIII and PstI.

The plasmid used in the experiments of in vitro transcription was pGEM1.

In the case of the cloning of the pGEM1 plasmid containing the sequence of pre-dianthin 30, the vector was digested with HindIII and BamHI, sites present in multicloning sites, and contemporaneously also the fragment coding for pre-dianthin 30, previously obtained by PCR amplification, was digested with BglII and HindIII. This allowed the ligation of the predianthin 30 fragment in the PGEM1 vector under the control of the T7 RNA polymerase promoter, the 5'-end of which was represented by BamHI/BglII and the 3'-end by the HindIII alone.

Figure 4:
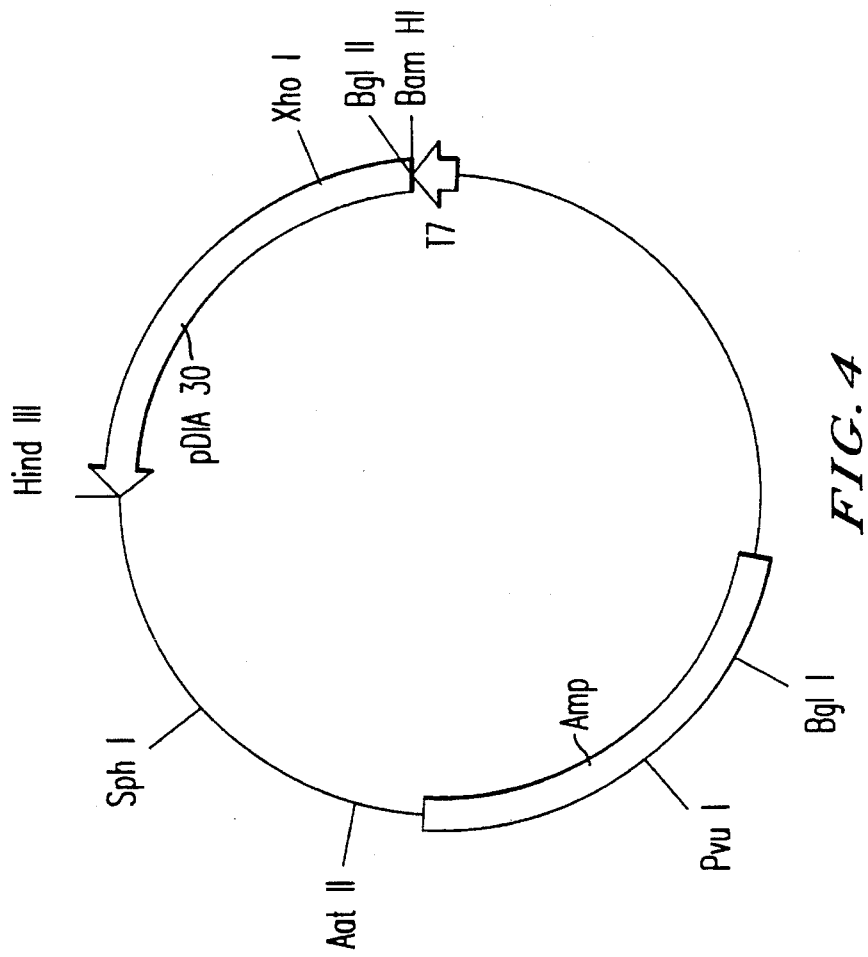

In the case of the fragment coding for dianthin 30 the digestions were, in sequence, NcoI and HindIII and the vector was digested as reported above. This allowed the ligation of the fragment at the 3'-end with the sequences HindIII whereas the ligation at 5' was preceded by an "end filling" reaction of the BamHI end of pGEMI and NcoI of the dianthin 30 fragment. The maps of the two constructs, named pGEM-pDia30 and pGEM-Dia30 respectively for pre-dianthin 30 and dianthin 30, are shown in FIGS. 4 and 5.

Biochemical characterization of the protein product

The m-RNA specific for the translation of predianthin 30 and dianthin 30 were transcribed using the above vectors. Transcription and in vitro translation were carried out as hereinafter reported.

In vitro transcription

The reaction mixture for carrying out an in vitro transcription included: 12 µl of Premix solution [consisting of (for a total volume of 6 ml) 1 ml of T-salts (20 mM spermidine, 400 mM HEPES, pH 7.5, 60 mM Mg-acetate; 100 µl of a solution of 50 mM each of CTP, ATP and UTP in 20 mM HEPES; 200 µl of 5 mM of GTP in 20 mM HEPES; 100 µl of 500 mM DTT; 100 µl of a 10 mg/ml BSA solution; 4.5 ml of sterile distilled water]; 0.5 µl of RNasin (recombinant inhibitor of RNase); 1 µl of CAP; 0.5 µl [$^{32}$P-UTP]; 2 µl linearized plasmidial DNA to be transcribed, 2 µl of RNA polymerase [SP6 or T7].

The reaction mixture was then incubated for 30 minutes at 40° C., after which 1 µl of an 8 mM solution GTP in 20 mM HEPES was added, followed by a second incubation of the same duration and temperature.

For the calculation of the incorporation percent of [$^{32}$P-UTP] the following method was used: 1 µl of the transcription mixture was sampled and 3 µl of sterile distilled water were added. 2 µl of the obtained solution were placed on two filters of DE81 (Whatman, USA) and they were dried in the air. Only one of the two filters was washed with 200 ml of a 0.15 M $Na_2HPO_4.12 H_2O$ solution for 2 minutes at room temperature for 4 times. It was washed twice with distilled water and twice with methanol.

The filter was dried in the air and the two filters were counted in a counter. The ratio between the counts resulting from the washed filter and that not washed gave the percent incorporation obtained in the transcription region.

In vitro translation

The system of rabbit reticulocytes was used. The reaction mix consisted of 137.5 µl 2 M KCl; 117.5 µl 40 mM magnesium acetate; 80 µl of a 10 mM tris-HCl solution, pH 7.4; 125 µl of an amino acid mixtures, except methionine at the concentration of 2 mM each; 155 µl of the "energy mix" mixture (4 mM GTP, 20 mM ATP in 0.4 ml 0.5 M tris-HCl, pH 7.5; the volume was adjusted to 1 ml with sterile distilled water and 80 mg of creatine phosphate were added, and finally 492.5 ml of sterile distiled water.

7 µl of Reaction Mix was then mixed with 2 µl of $^{35}$S-methionine, 1 µl RNA and 10 µl of rabbit reticulocytes lysate (Promega, USA) treated or not with nuclease. The mixture was incubated for 1 hour at 30° C. The proteins obtained and labelled with radioactive methionine were analyzed by SDS-PAGE.

We claim:

1. A DNA sequence coding for a ribosome inactivating protein from *Dianthus caryophyllus* as shown in SEQUENCE ID NO: 1.

2. A DNA sequence coding for a ribosome inactivating protein from *Dianthus caryophyllus* as shown in SEQUENCE ID NO: 2.

3. A cloning vector comprising the DNA sequences of claims 1 or 2.

4. An expression vector comprising the DNA sequences of claims 1 or 2.

5. A vector according to claim 4 which is the plasmid pKK-DIA 30 obtainable from the *E. coli* strain NCTC 12477.

6. A vector according to claim 4 which is the plasmid pGEM-oDIA 30 obtainable from the *E. coli* strain NCTC 12693.

7. An host cell transformed by the vectors of claims 5 or 6.

8. *E. coli* strains NCTC 12477 and 12693.

* * * * *